(12) United States Patent
Bertram, III

(10) Patent No.: US 9,833,249 B2
(45) Date of Patent: Dec. 5, 2017

(54) BONY BALANCING APPARATUS AND METHOD FOR TOTAL KNEE REPLACEMENT

(76) Inventor: Morton Bertram, III, Naples, FL (US)

(*) Notice: Subject to any disclaimer, the term of this patent is extended or adjusted under 35 U.S.C. 154(b) by 385 days.

(21) Appl. No.: 13/635,212

(22) PCT Filed: Aug. 17, 2012

(86) PCT No.: PCT/US2012/051393
§ 371 (c)(1),
(2), (4) Date: Sep. 14, 2012

(87) PCT Pub. No.: WO2013/032741
PCT Pub. Date: Mar. 7, 2013

(65) Prior Publication Data
US 2014/0249534 A1    Sep. 4, 2014

Related U.S. Application Data

(63) Continuation-in-part of application No. 13/220,143, filed on Aug. 29, 2011.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/17* | (2006.01) | |
| *A61B 17/15* | (2006.01) | |
| *A61B 90/00* | (2016.01) | |

(52) U.S. Cl.
CPC ........ *A61B 17/1764* (2013.01); *A61B 17/155* (2013.01); *A61B 2090/062* (2016.02)

(58) Field of Classification Search
USPC .................................................. 606/86 R–89
See application file for complete search history.

(56) References Cited

U.S. PATENT DOCUMENTS

| | | |
|---|---|---|
| 3,941,127 A | 3/1976 | Froning |
| 4,058,114 A | 11/1977 | Soldner |
| 4,360,028 A | 11/1982 | Barbier et al. |
| 4,436,684 A | 3/1984 | White |
| 4,440,168 A | 4/1984 | Warren |
| 4,583,538 A | 4/1986 | Onik et al. |
| 4,703,751 A | 11/1987 | Pohl |
| 4,841,975 A | 6/1989 | Woolson |
| 5,364,401 A | 11/1994 | Ferrante et al. |
| 5,611,802 A | 3/1997 | Samuelson et al. |

(Continued)

FOREIGN PATENT DOCUMENTS

EP        0466659        1/1992

*Primary Examiner* — Sameh Boles
(74) *Attorney, Agent, or Firm* — John G. Posa; Belzer PC

(57) ABSTRACT

Total knee replacement surgery is improved through custom cuts on the distal femur without resorting to expensive computer navigation. The method involves measurements on plain radiographs or CT scans prior to surgery, the amount of bone that would be resected on each knee, medially and laterally on the distal femur. In the preferred embodiments, the predetermined distance is in the range of 8-12 mm, more preferably 10 mm, and the resulting distance from the second line to the apex of the lateral condyle is in the range of 6 to 7 mm. A cutting fixture is provided and used to resect the medial condyle at the predetermined distance and the lateral condyle at the measured resulting distance.

6 Claims, 10 Drawing Sheets

(56) References Cited

U.S. PATENT DOCUMENTS

| | | | |
|---|---|---|---|
| 5,624,444 A | 4/1997 | Wixon et al. |
| 5,824,100 A | 10/1998 | Kester et al. |
| 6,077,270 A | 6/2000 | Katz |
| 6,695,848 B2 | 2/2004 | Haines |
| 6,702,821 B2 | 3/2004 | Bonutti |
| 7,060,074 B2 | 6/2006 | Rosa et al. |
| 7,104,996 B2 | 9/2006 | Bonutti |
| 7,104,997 B2 | 9/2006 | Lionberger et al. |
| 7,141,053 B2 | 11/2006 | Rosa et al. |
| 7,156,853 B2 | 1/2007 | Muratsu |
| 7,344,541 B2 | 3/2008 | Haines et al. |
| 7,458,989 B2 | 12/2008 | Banks et al. |
| 7,534,263 B2 | 5/2009 | Burdulis, Jr. et al. |
| 7,618,421 B2 | 11/2009 | Axelson, Jr. et al. |
| 7,628,793 B2 | 12/2009 | Calton et al. |
| 7,632,283 B2 | 12/2009 | Heldreth |
| 7,678,115 B2 | 3/2010 | D'Alessio, II et al. |
| 7,708,740 B1 | 5/2010 | Bonutti |
| 7,749,229 B1 | 7/2010 | Bonutti |
| 7,780,671 B2 | 8/2010 | Berger et al. |
| 7,815,645 B2 | 10/2010 | Haines |
| 7,959,635 B1 | 6/2011 | Bonutti |
| 7,967,822 B2 | 6/2011 | Haines et al. |
| 7,981,158 B2 | 7/2011 | Fitz et al. |
| 8,062,302 B2 | 11/2011 | Lang et al. |
| 8,062,377 B2 | 11/2011 | Haines |
| 8,066,708 B2 | 11/2011 | Lang et al. |
| 8,070,752 B2 | 12/2011 | Metzger et al. |
| 8,083,745 B2 | 12/2011 | Lang et al. |
| 8,105,330 B2 | 1/2012 | Fitz et al. |
| 8,122,582 B2 | 2/2012 | Burdulis, Jr. et al. |
| 2005/0038442 A1 | 2/2005 | Freeman |
| 2005/0102032 A1 | 5/2005 | Beynnon et al. |
| 2005/0234461 A1 | 10/2005 | Burdulis et al. |
| 2008/0281329 A1 | 11/2008 | Fitz et al. |
| 2010/0174287 A1 | 7/2010 | Walker et al. |
| 2010/0222783 A1 | 9/2010 | May et al. |
| 2010/0228257 A1 | 9/2010 | Bonutti |
| 2011/0029116 A1 | 2/2011 | Jordan et al. |
| 2011/0112542 A1 | 5/2011 | Gross |
| 2011/0208093 A1* | 8/2011 | Gross et al. ............... 600/587 |

\* cited by examiner

US 9,833,249 B2

BONY BALANCING APPARATUS AND METHOD FOR TOTAL KNEE REPLACEMENT

REFERENCE TO RELATED APPLICATION

This application is a continuation-in-part of U.S. patent application Ser. No. 13/220,143, filed Aug. 29, 2011, the entire content of which is incorporated herein by reference.

FIELD OF THE INVENTION

This invention relates generally to total knee replacement and, in particular to surgical techniques and instrumentation to more precisely balance the knee joint.

BACKGROUND OF THE INVENTION

In classical arthroplasty alignment, the distal femoral cut is perpendicular to the femoral mechanical axis. This axis is defined as a line drawn through the center of the femoral head to the center of the knee, which is defined by the center of the intercondylar notch, with the patient standing and weight bearing. Under current practice, most surgeons prefer a zero degree cut; that is, a perpendicular cut on the tibia. This is a line from the center of the tibial anatomy, which is at the center of the tibial spines, to the center of the talus. The goal here is a right angle cut to that alignment axis. When these two landmarks are combined, the result should be a well-balanced knee in the coronal plane, meaning with the knee in full extension at 30 and 60 degrees of flexion. There should also be minimal to trace laxity in that knee on examination at the time of the arthroplasty procedure.

Historically, if the alignment is not appropriate and there is imbalance present after the bone cuts have been made, most surgeons assume that there are problems with the soft tissue balancing and that there are contractures of the medial or lateral structures which are preventing perfect balancing of the knee. While this may be true in a small portion of knees with significant combined sagittal and coronal deformity, I believe that improper bone cuts are the problem and not ligament balancing. I believe this is true in 95 percent of total knee replacement cases.

Currently, most surgeons use instrumentation which has been around for approximately 40 years. Using these instruments on the femoral side, surgeons first position an intramedullary rod, which is inserted through a hole drilled in the distal femur. After the rod is placed, a five degree valgus alignment for the cuts on the distal femur is arbitrarily and traditionally chosen for most male patients. This five degree valgus alignment is chosen because typically in men the difference between the anatomic axis, which is the line drawn up the femoral shaft to the center of the femur, and the mechanical axis, which is the line drawn from the center of the femoral head to the center of the femur is roughly five degrees. This difference in women it is approximately seven degrees. Thus, when using the intramedullary alignment on the femur, this angle is chosen for the cut on the distal femur to achieve proper alignment.

However, as learned from computer navigation, these historically elected angles may be inappropriate most of the time. Some patients may exhibit 3.8 degrees of valgus in their alignment, others may be 7.3. The fact is, true accuracy can never be realized with an educated guess. Computer navigation is perhaps the most accurate way to make this cut. Navigated procedures actually locate the center of the femoral head based on complex mathematic algorithms, and "registration points" on the bones taken at the time of surgery, using existing, identifiable landmarks. However, computer navigation is expensive, it is time consuming, and it will probably not ever be available to every surgeon.

SUMMARY OF THE INVENTION

This invention improves upon total knee replacement surgery by facilitating custom cuts on the distal femur and/or tibia without resorting to expensive computer navigation. The method involves measurement, on plain radiographs of computerized tomographic (CT) scans prior to surgery, the amount of bone that would be resected on each knee, medially and laterally on the distal femur, based upon the perpendicular measurement from the center of the femoral head to the center of the intercondylar notch. The anatomy of each patient is unique, and each requires a unique amount of resection. In the event of extreme bowing or deformity, the technique may always be augmented with the knowledge and skill of the surgical team.

The method begins with obtaining an image of a patient's femur, the image including a hip joint with a femoral head and a knee joint with medial and lateral condyles and an intercondylar notch. A first line is identified on the image from the center of the femoral head to the center of the distal femur and the intercondylar notch. A second line is traced perpendicular to the first line, the second line being at a predetermined, arbitrary distance from the apex of the medial condyle, preferably 8-10 mm. The resulting distance from the second line to the apex of the lateral condyles may then be read off of the image.

An inventive cutting fixture is provided and used to resect the medial condyle at the predetermined distance and the lateral condyle at the measured resulting distance. In the preferred embodiments, the predetermined distance is in the range of 8-12 mm, more preferably 10 mm, and the resulting distance from the second line to the apex of the lateral condyle is typically in the range of 6 to 7 mm. Based upon clinical research, the amount removed from the lateral condyle is in the range of 3-4 mm less than the medial side.

The cutting fixture may be initially rotatable to first adjust for the predetermined distance, and/or may further include an arm configured for placement on the outer cortex of a femur. The cutting fixture includes at least one cutting slot and one or more devices for measuring the distance between the apex of the medial condyle and the slot for resecting the medial condyle and for measuring the distance between the apex of the lateral condyle and the slot for resecting the lateral condyle. In some embodiments the cutting fixture may include two separate slots, one for resecting the medial condyle and the other for resecting the lateral condyle. In all embodiments, however a mechanism ensures that the medial and lateral cuts are at all times co-planar and substantially perpendicular to the mechanical axis of the femur, barring any deformations or other atypical physical circumstances.

DETAILED DESCRIPTION OF THE INVENTION

Figure 1:
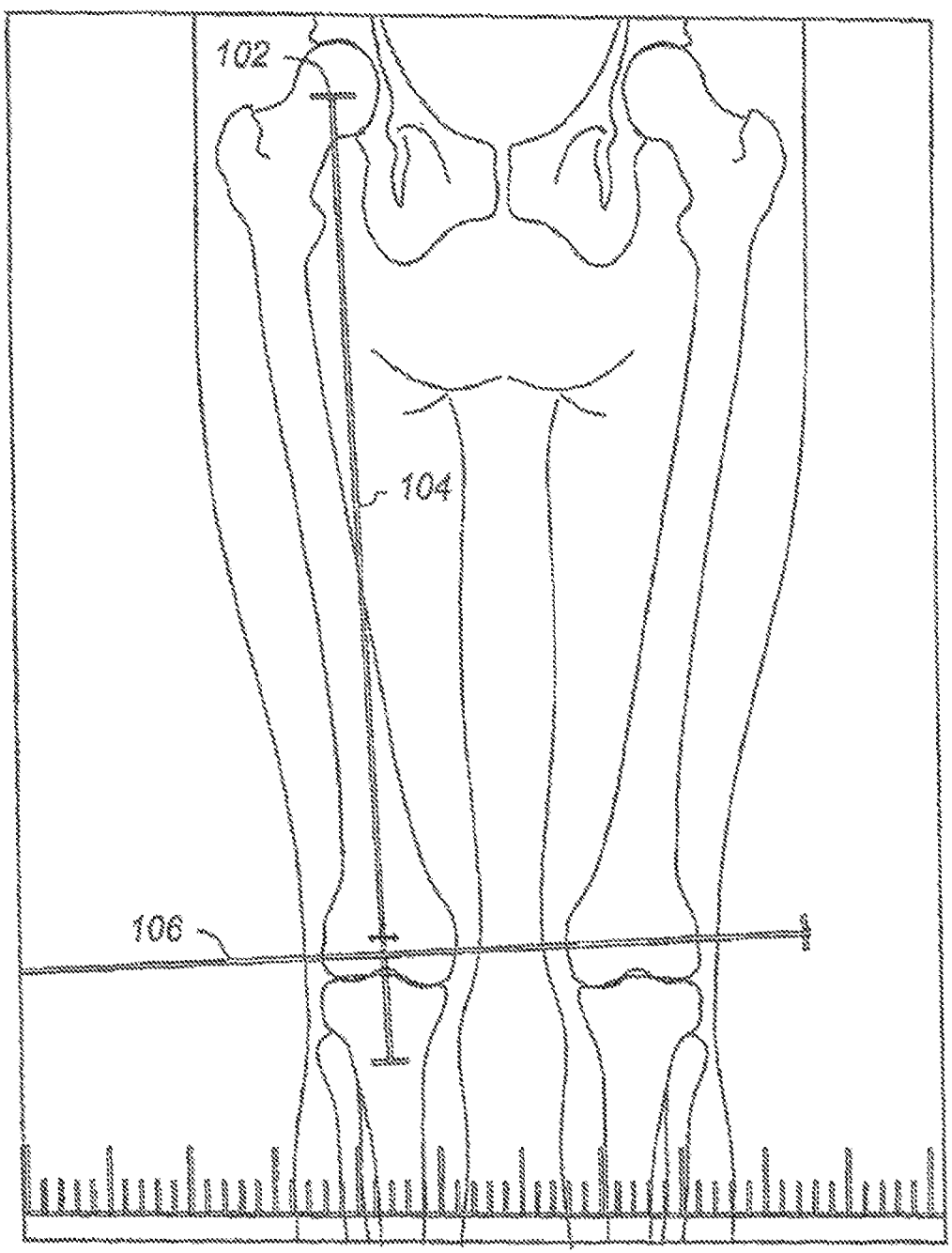
FIG. 1 depicts a portion of 3-foot digital standing x-ray used for measurement.

This invention resides in apparatus and methods enabling custom cuts on the distal femur without resorting to expensive computer navigation. The method involves measurement, on an x-ray image or CT scan prior to surgery, the amount of bone that would be resected on each knee, medially and laterally on the distal femur, using a five degree valgus cut. The amount of bone to be resected with this predicted cut is then compared intraoperatively to what we find when we actually make the cuts.

A digital x-ray with the patient standing may be taken from hip, including the knee and the foot, on one film. A line is then drawn from the center of the femoral head to the center of the distal femur and the intracondylar notch. A perpendicular is taken to this line, with a reference point of 10 mm of resection taken arbitrarily from the medial side. This typically gives a resection somewhere in the 5 to 7 mm range on the lateral side, but this may be different for each patient. From my own personal experience, the "best" knees have 3-4 mm less resected on the lateral distal femur compared to the medial side. This measurement could be made and the measurement that would be obtained would then be 'reverse engineered' at the time of surgery.

When using a preoperative CT (computerized tomography) scan, the radiologist takes a scout film from the femoral head to the talus distally. First a line is drawn from the .center of the femoral head, using reformatted information, to find the exact center of the femoral head, to the center of the intercondylar notch distally. This represents the true center of the distal femur and knee joint. The reformatted information is derived from combining coronal and transverse plane data.

The surgeon provides the radiologist with the amount of bone he or she prefers to be removed from the distal femur medially. Again, this will typically be in the range of 8-12 mm. This line is then superimposed on the distal femur medially, and an orthogonal measurement tool is used to make a perpendicular line to the superimposed line from the center of the femoral head to the center of the intercondylar notch. A linear measurement tool is then used to place the orthogonal line exactly the distance the surgeon has chosen from the medial distal femoral apex. The exact place to measure the distal medial femur has again been chosen based on reformatted information from the scan through the distal femur.

Now the orthogonal line is viewed as it crosses the lateral distal femur. The linear measurement tool is now used to measure the distance from the orthogonal line to the lateral distal femur apex. Now we have established the measurements needed to cut from the distal femur to establish our patient unique mechanical axis. An inventive cutting device is pinned on the distal femur and the cuts are made, usually in accordance with a collaborative effort on the part of the radiologist and the surgeon.

For the tibial cuts, the radiologist uses the same technique on the tibia. A line is drawn from the center of the tibial spines proximally to the center of the tibial plafond distally. The orthogonal line is now used to reference via the linear measurement tool the amount of bone to be removed from the medial tibial plateau. The center of the medial tibial plateau is determined again from reformatted information. Once again the surgeon has provided the radiologist with the amount of bone he or she desires to be cut from the medial tibial plateau. Depending upon the deformity and the surgeon preference, the measurement here may be made from the medial or lateral tibia. Whichever approach is chosen, the radiologist then gives the surgeon the opposite linear measurement to complete the data set.

The method uses an inventive cutting block that is pinned on the distal femur and adjusted to perform the resections on both sides. On the medial side, the goal would be 10 mm, more or less. Longer distances in the range of 10-12 mm, or shorter distances in the range of 5-9 may sometimes be used depending upon anatomy. On the lateral side, the depth of the cut is based on the image measurements. This procedure should achieve ideal coronal balance for that patient.

FIG. 1 depicts a portion of 3-foot digital standing x-ray used for measurement. A point 102 in the center of the femoral head is marked as shown, and a line 104 is drawn from the center of the femoral head to the center of the knee using the tools for measuring the digital films available on most digital software programs. This line, from the center of the hip to the center of the knee, defines the "mechanical axis" of the knee. An "orthogonal measurement tool" is used to draw a line 106 perpendicular to line 104. This line is then placed at the level of the knee to determine how much bone should be resected in accordance with the invention.

Figure 2:
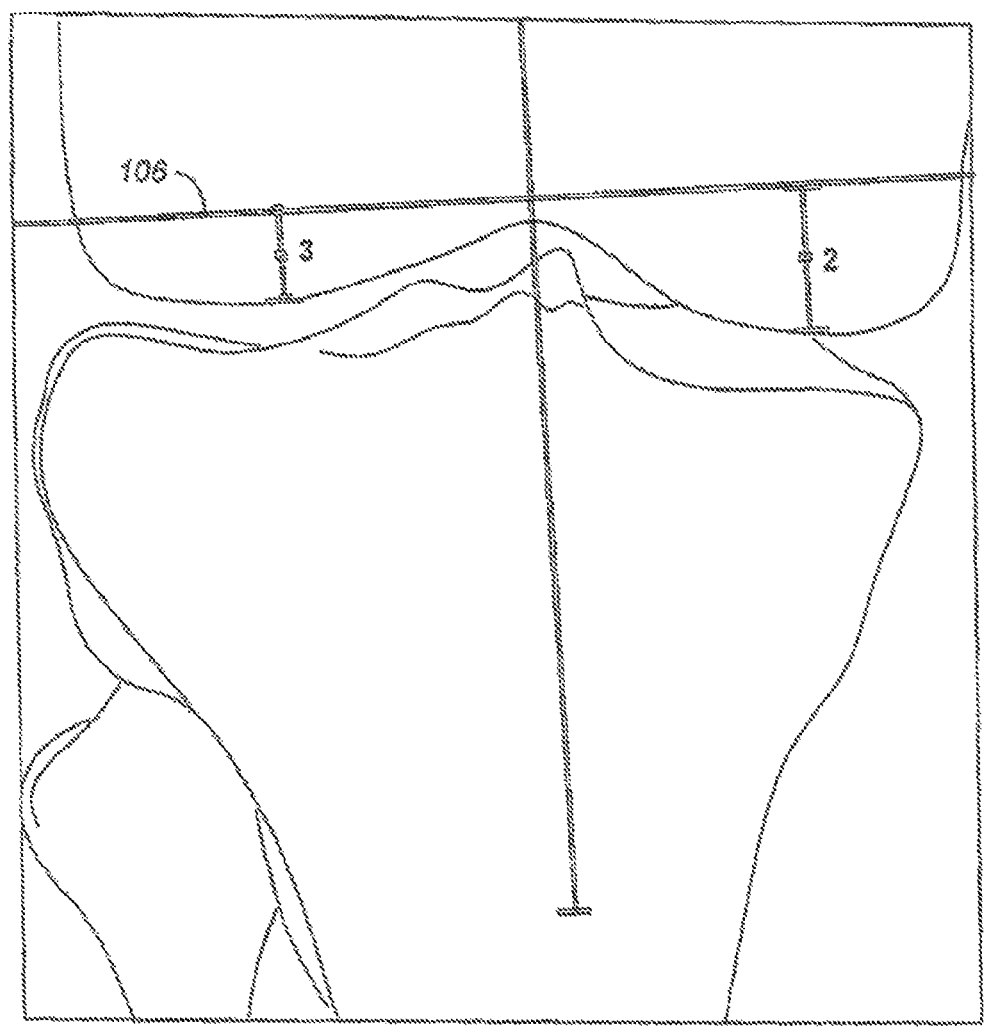
FIG. 2 is a closer view of the line shown in FIG. 1.

FIG. 2 is a closer view of the line shown in FIG. 1. Ten (10) millimeters (mm) is measured from the medial femoral condyle as shown by the line marked "2." The distance from the lateral femoral condyle is then measured using the calibrated measuring tool on the computer software. The line labeled "3" shows the measurement of the predicted cut of the lateral femoral condyle along the line 106 perpendicular to the mechanical axis, thereby establishing the correct cut for the mechanical axis of this patient's unique anatomy. In this case, the measurement of lines 2 and 3 turns out to be 10 mm and 6.6 mm, respectively. This measurement will predetermine the cuts for the distal femur at the time of surgery to achieve the correct alignment for this patient.

To make these cuts based on the predicted values involves the use of a unique cutting block and system. This system and instrument allows the measured resection to take place medially and laterally. By convention, the medial resection may be either 8 or 10 mm. The lateral resection will be variable, however, and will be determined by the value arrived at by analysis of the digital film lateral femoral condyle cut.

Figure 3:
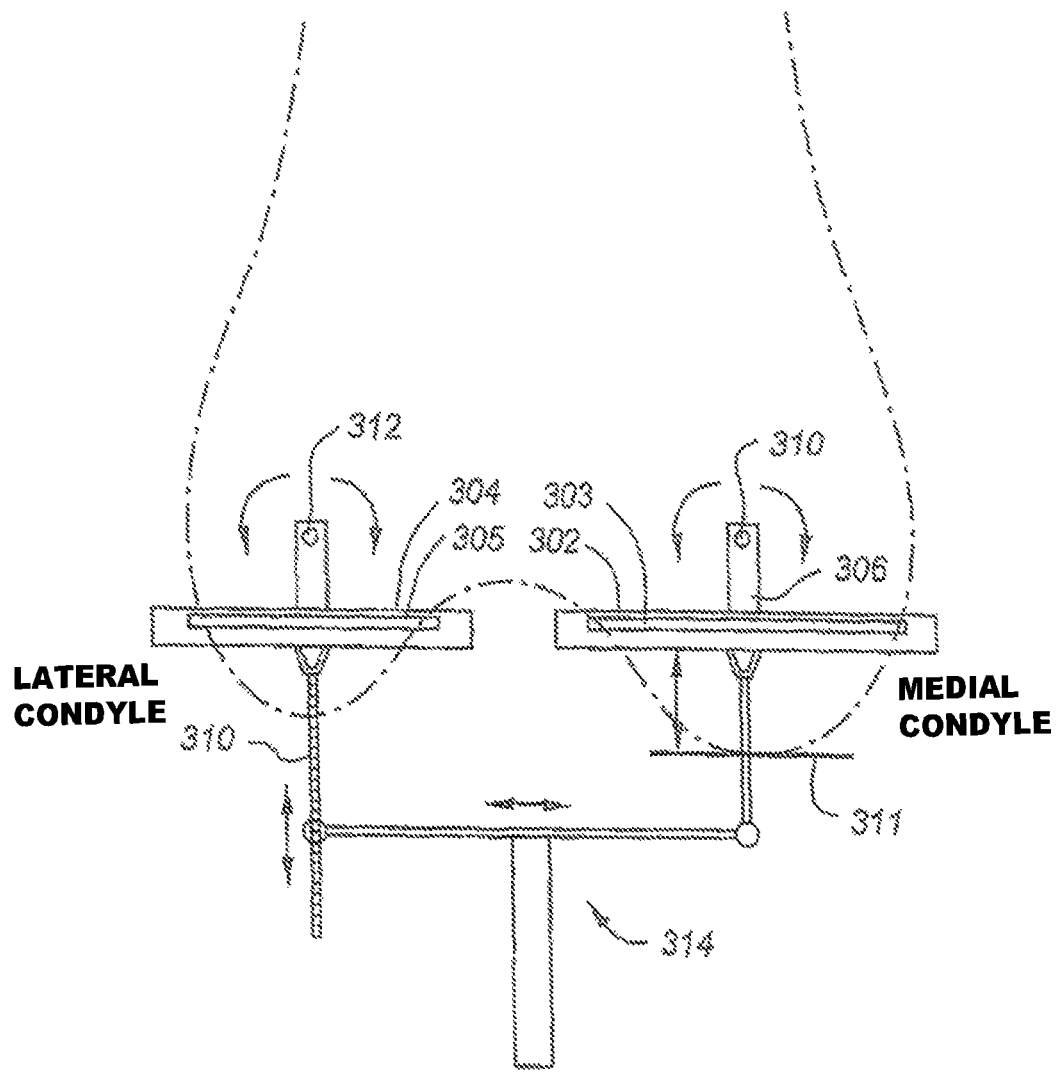
FIG. 3 illustrates one embodiment of a cutting fixture constructed in accordance with the invention.

FIG. 3 illustrates one embodiment of a cutting fixture constructed in accordance with the invention. The system includes a medial cutting guide 302 with a first saw-receiving slot 303. The medial guide 302 includes a fixation feature such as a pinhole 310 coupled to the guide through link member 306. The use of a pinhole enables the guide to rotate about point 310. The medial guide 302 further includes a stop element 311 which, when positioned against the most, lateral aspect (i.e., apex) of the medial condyle, fixes the cutting slot at a fixed distance such as 8 or 10 mm.

The medial guide 302 is interconnected to a lateral cutting guide 304 having slot 305 through a linkage 314. The linkage 314 enables the lateral guide 304 to be moved toward and away from the medial guide 302, and adjusted in the proximal-to-distal dimension while at all times keeping the cutting slots 303, 305 coplanar to one another.

One portion of the distal guide 304 includes a proximal-to-distal depth gauge 320 which measures the depth of the lateral cut. This guide is adjusted to match the correct depth of cut measured from the using the calibrated measuring tool on the computer software as discussed above. In the disclosed example, the depth would be adjusted to read 6.6 mm, at which point the lateral guide would be pinned in position at 312. A caliper may also be used to measure the amount of bone to be resected from the lateral side. The slots are checked to ensure that they are co-planar, after which both cuts are made.

Figure 4:
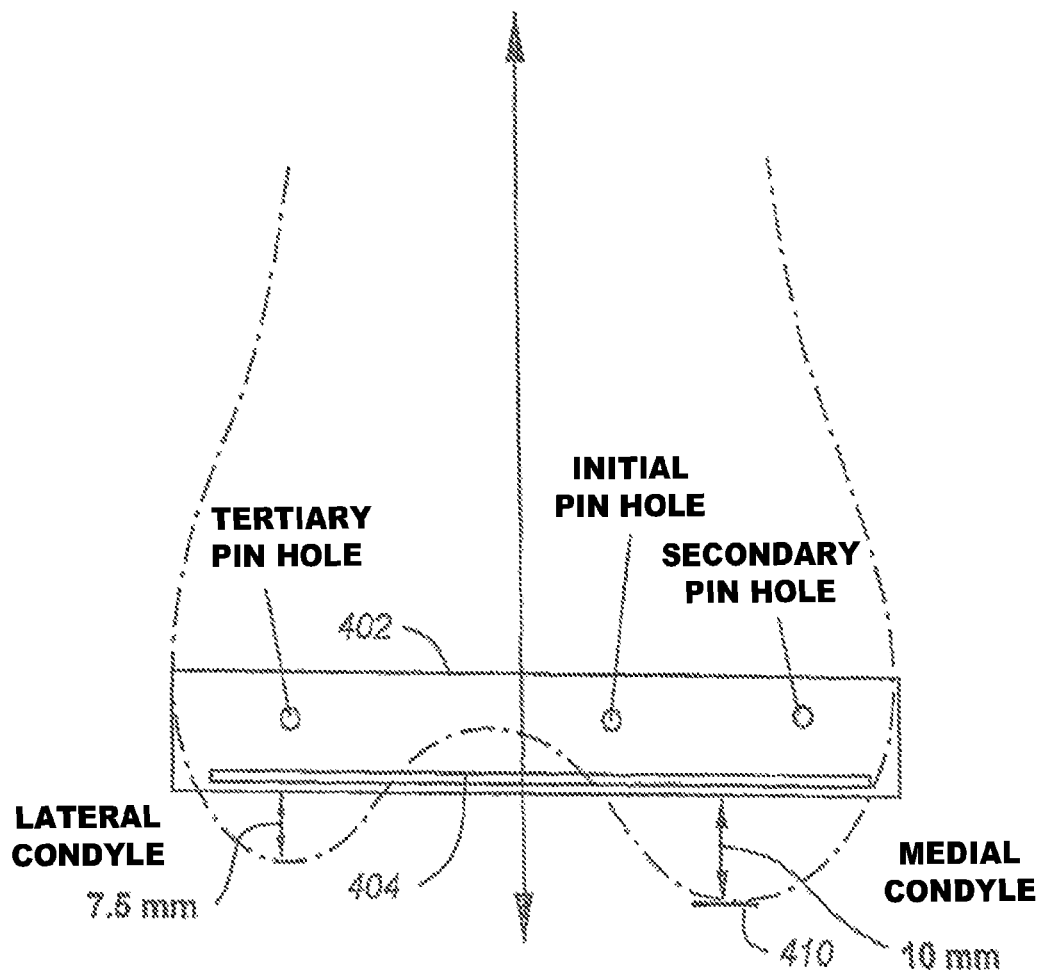
FIG. 4 shows an embodiment of a cutting block that uses a single slot and a plurality of pin holes.

FIG. 4 shows an embodiment of a different cutting block 402 that uses a single slot 404 and a plurality of pin holes. The block 402 is first pinned in an initial hole aided by a stylus 410 which is temporarily placed medially in the slot to show a predetermined distance such as 8-10 mm. As with the embodiment of FIG. 3, the block is rotated about the initial pin hole until the correct distance is shown on the lateral side (i.e., 6.6 mm in the disclosed example). The stylus 410 may be moved over and used for this measurement as well. Once the two distances are correct the cuts are made.

Figure 5A:
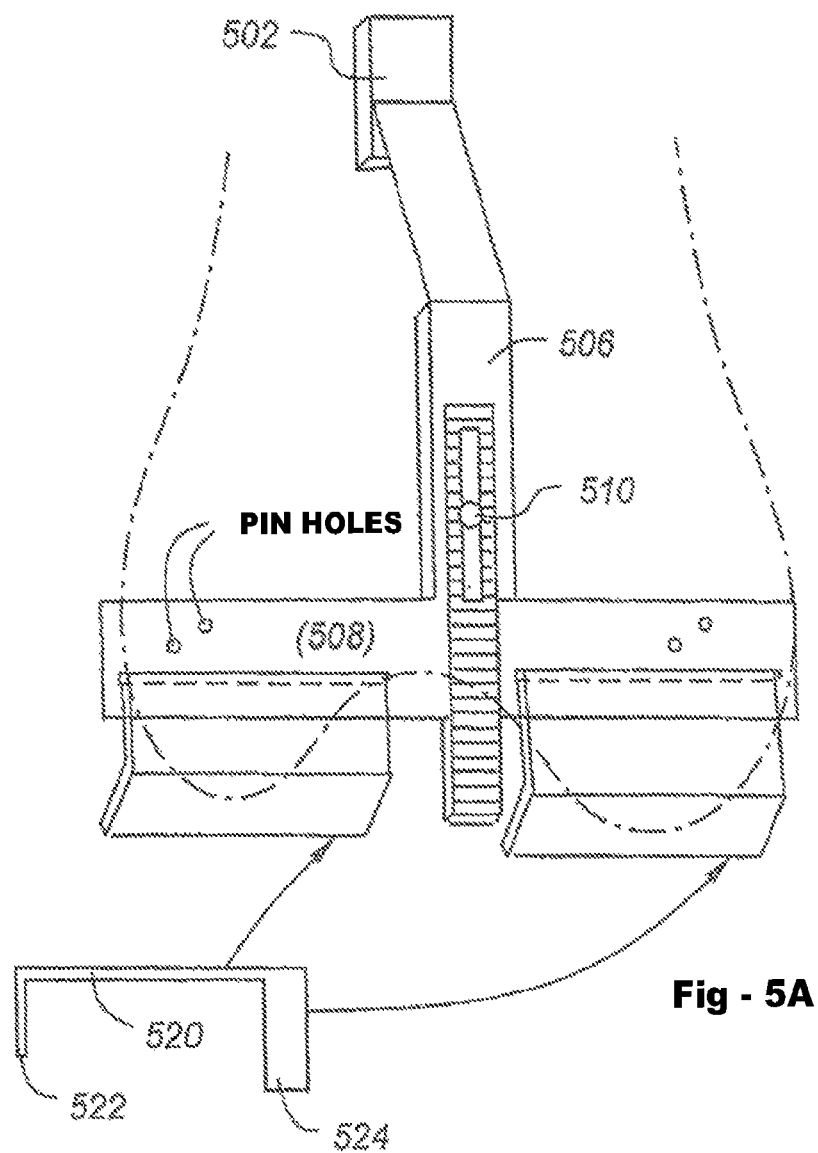
FIGS. 5A and 5B present a series of drawings which show how the cutting block may be placed manually on the distal femur.
Figure 5B:
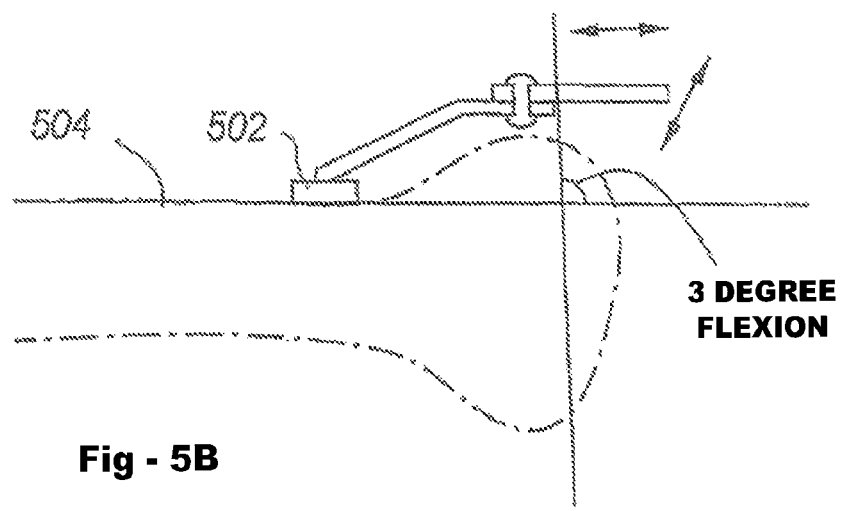

FIGS. 5A and 5B present a series of drawings which show how the cutting block may be placed manually on the distal femur. FIG. 5A is a side view of the apparatus, and FIG. 5B is a top-down view. In this case the flexion/extension of the block will be determined by a 'foot' 502 that fits on the anterior cortex 504. This anterior cortex reference provides the flexion/extension of the cut, adding three degrees of flexion to avoid notching of the distal femoral cortex. The guide includes a first arm 506 that attaches to the cutting block portion 508 through an adjustable slot 510 that facilitates proximal-distal excursion as well as rotation to swing varus or valgus. One or more stylus components 520 may be provided with a first end 522 that fits into the slot 512 of the cutting block and a second end that rests against the apex of a given condyle. The second end 524 may vary in thickness to give cuts of, say, 4-12 mm in 1 mm increments. The proximal-distal adjustment allows different thicknesses of cuts to be made based on the thickness of the predetermined sizes.

In use, a stylus component would be placed in the medial slot to resect at a given distance such as 8-10 mm, continuing the disclosed example. The correct distance for the later side (i.e., 6.6 mm in this case) could either be measured or a second stylus component having the correct dimensions could be used. Once the medial and lateral distances have been set in conjunction with varus or valgus adjustment, the cutting block portion 508 is pinned with pin holes 516 and the cuts are made.

Figure 6A:
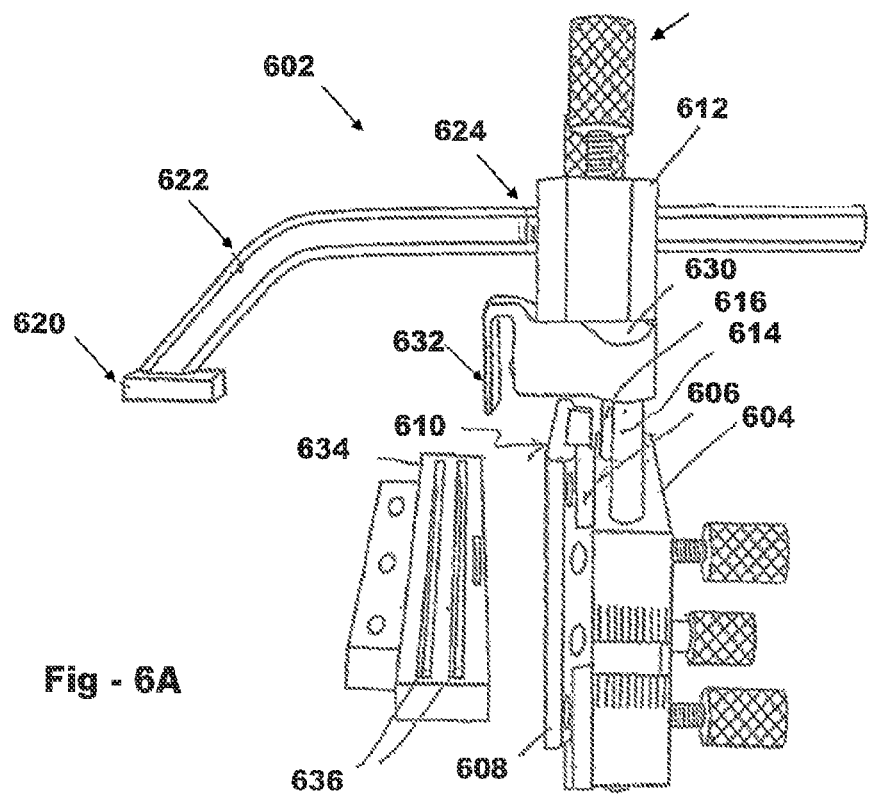
FIG. 6A is a perspective view of more comprehensive instrumentation constructed in accordance with the invention to perform the resections prescribed herein.

FIG. 6A is a perspective view of preferred instrumentation constructed in accordance with the invention to perform the distal femoral resections prescribed herein. The instrumentation 602 includes a block 604 coupled to a slide plate 606 forming a "swinging gate" described in further detail below. The slide plate 606 is received by a contact plate 608 having a surface 610 adapted to contact the apex of the distal femur on the medial side. The block 604 is coupled to a body 612 via rods 614, 616, enabling the body 612 to move up and down relative to the block 604. A rod 622 is journaled through the body 612, terminates at one end in a "foot" 620 adapted for placement against the anterior cortex of the distal femur as shown in subsequent drawings.

The rod 622 slides within body 612 with knob 626 being used to lock the rod in position. Markings 624 may be provided on the rod 622 to indicate the advancement thereof. The body 612 is further coupled to a component 630 having a connector 632 to receive a cutting block 634 having one or more slots 636 to receive a cutting device such as an oscillating saw (not shown) to perform the distal femoral resection. The components that contact bone, including cutting block 634, contact plate 608 and foot 620 may all include apertures to receive pins to temporarily secure that component relative to the bone. All of the various components are preferably constructed of metal though hard plastics and other materials may alternatively be used.

Figure 6C:
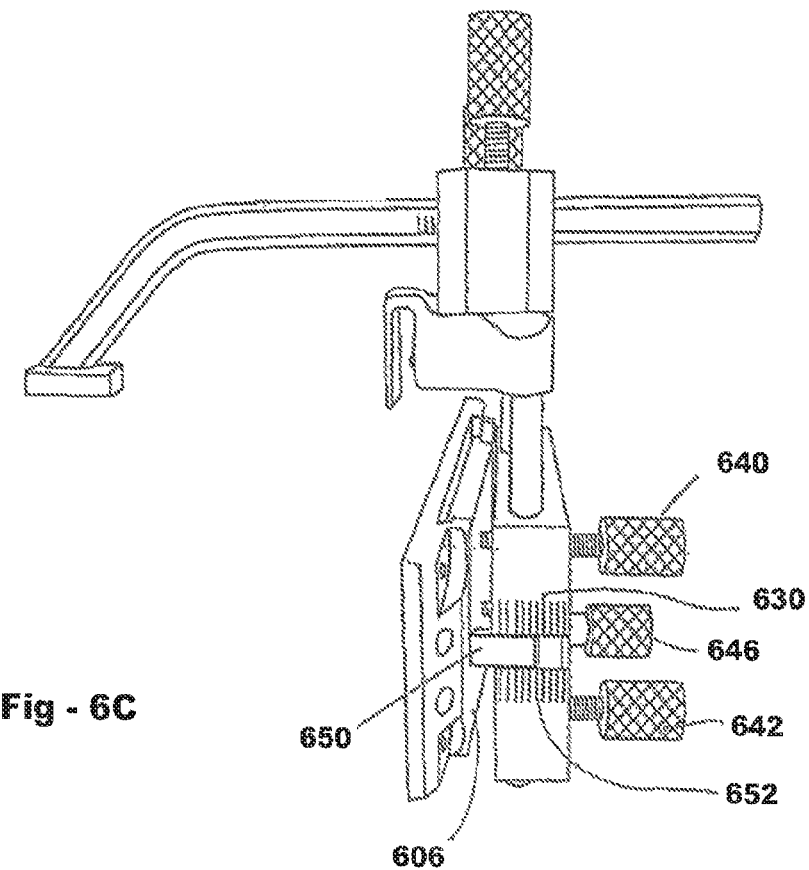
FIG. 6C is a perspective view of the instrumentation showing how the gate has been swing open and locked into position.
Figure 6B:
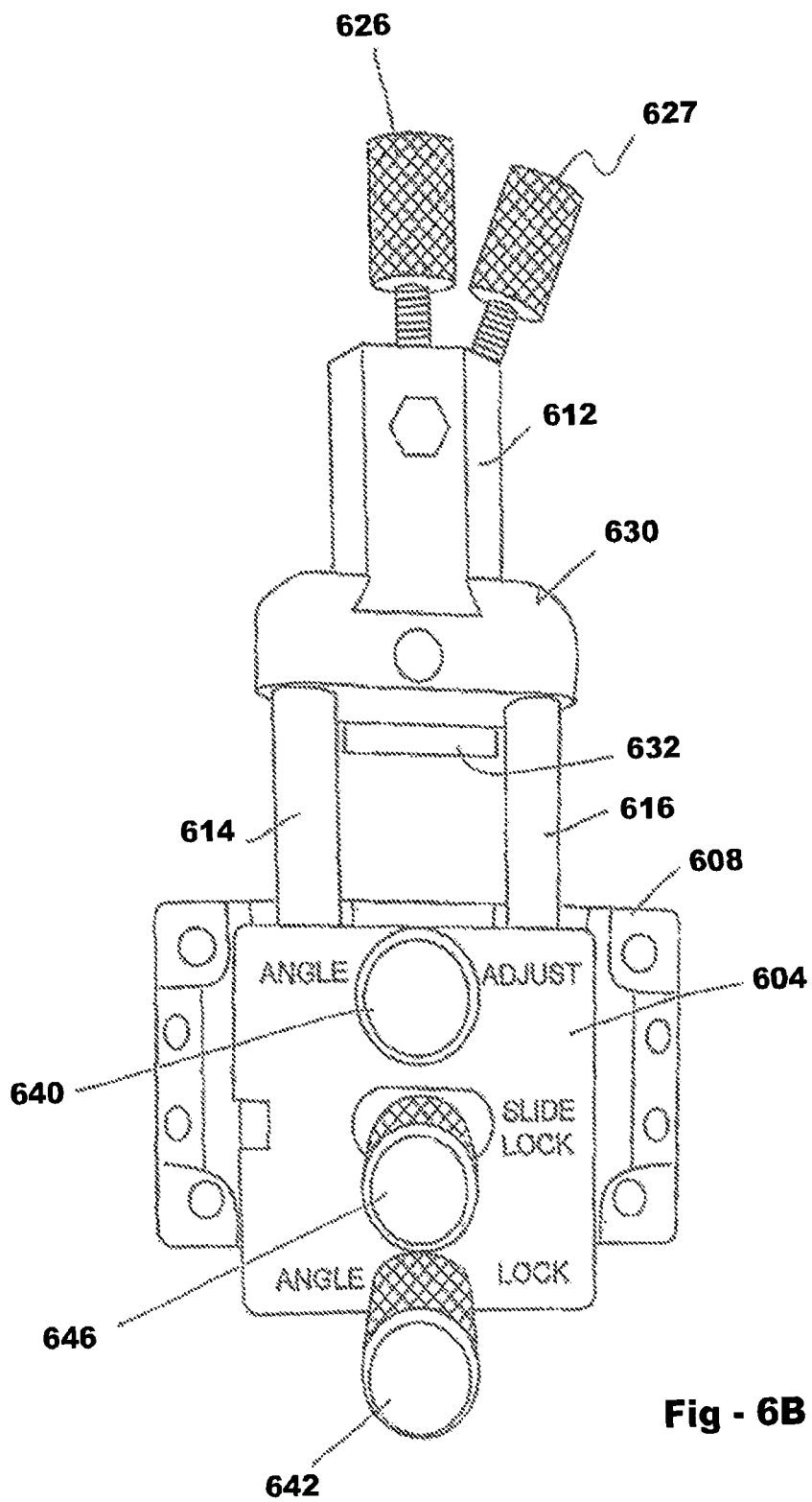
FIG. 6B is a front, view of a block showing various adjustment mechanisms.

FIG. 6B is a front view of the block 604 with rod 622 removed showing various adjustment mechanisms. In particular, a first knob 640 is used to adjust the angle of the swinging gate, with knob 642 being used to lock that angle in position. Knob 646 is used to lock into position the relative up-down sliding movement of plates 60 and 608. An additional knob 627 may be provided to rotate the entire assembly by 15 degrees, more or less, to ensure that foot 620 may be pinned to an optimally conformal bone surface.

FIG. 6C is a perspective view of the instrumentation showing how the gate has been swing open using knob 640 and locked into position using knob 642. Note that as the gate swings, a slug 650 coupled to slide plate 606, enabling an angle measurement to read from of a set of markings 652. This reading indicates the amount of bone that will be removed, always on the lateral side.

Figure 7A:
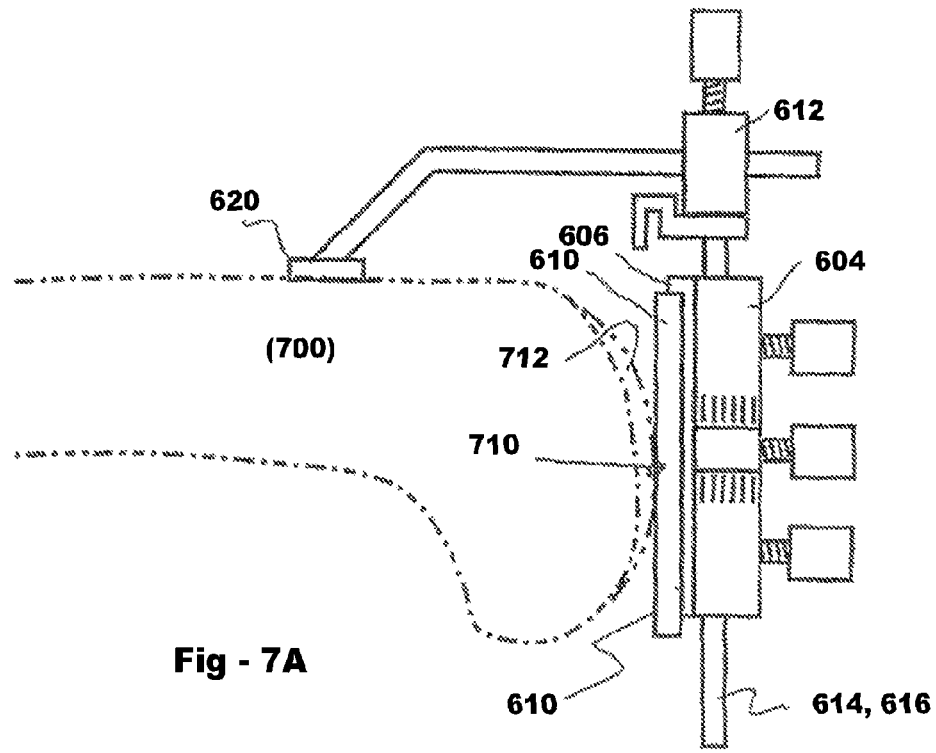
FIG. 7A begins a series of illustrations that show how the instrumentation of FIG. 6 is used to resect the distal femur.

FIG. 7A begins a series of illustrations that show how the instrumentation of FIG. 6 is used to resect distal femur 700 according to the invention. In FIG. 7A, the foot has been pinned to the anterior cortex of the distal femur, as shown. It is typically desirable to pin the foot in position initially then assemble the other components as needed to the pinned foot. Also in FIG. 7A, body 612 has been moved axially and block 604 along with slide plate 606 and contact plate 610 have been moved and locked into position so that surface 610 contact the apex 710 of medial condyle 712. Though not shown in the drawings, a separate set of knobs may optionally be provided on block 604 to lock the sliding movement of the block along rods 614, 616.

Figure 7B:
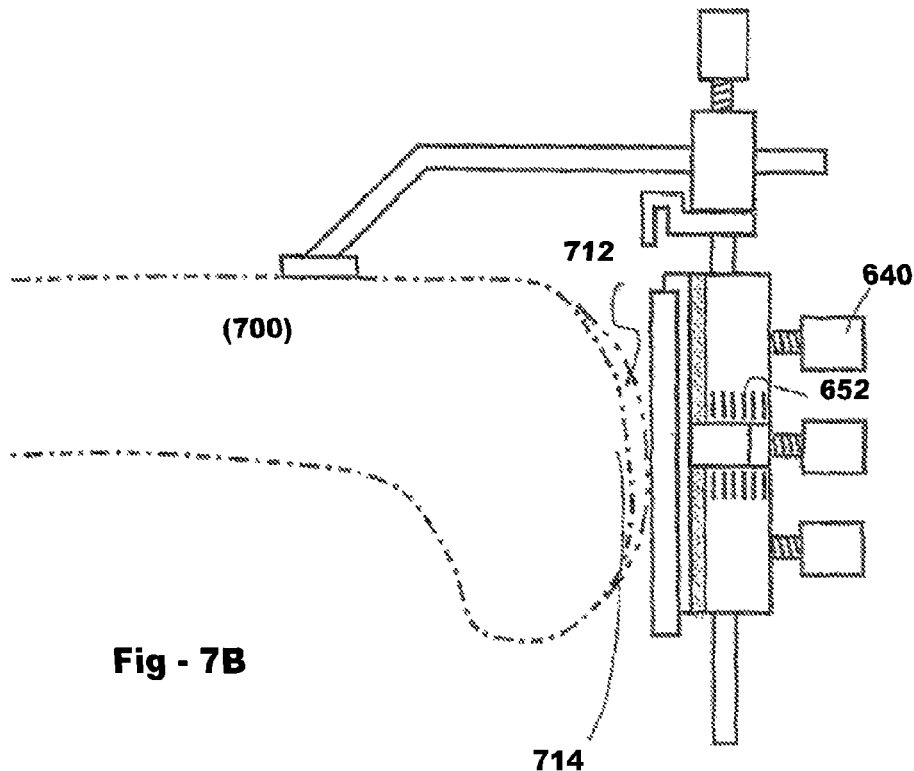
FIG. 7B shows how a knob has been adjusted so that an indicator reads the desired amount of bone to be resected from the distal femoral condyle as indicated form the radiograph(s) in accordance with the method of the invention.
Figure 7C:
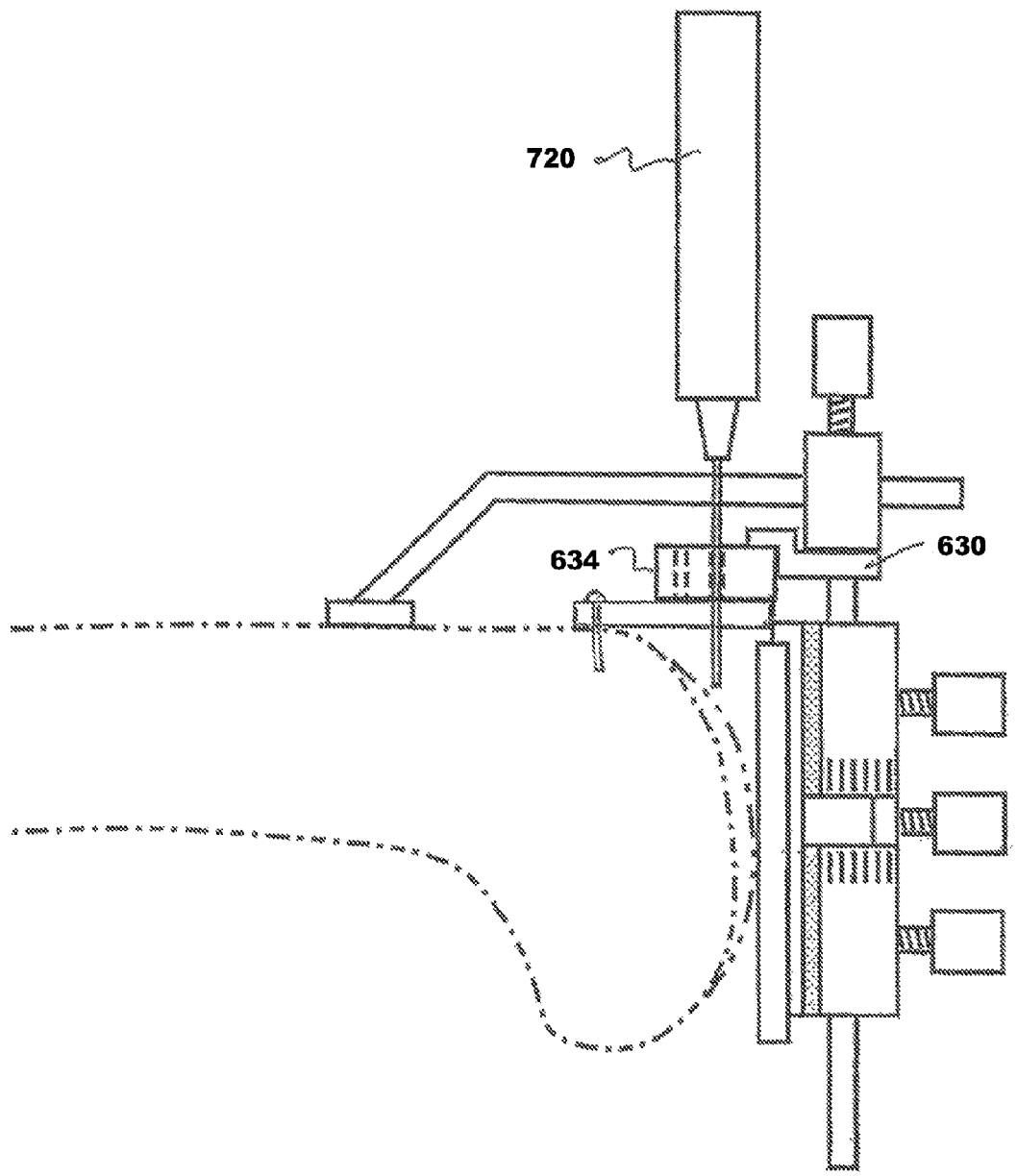
FIG. 7C illustrates the assembled apparatus locked into position and/or pinned into place, with a cutting block and tool being used to resect the distal femur to achieve a balanced knee without the need for expensive computer navigation.

In FIG. 7B, knob 640 has been adjusted so that indicator 652 reads the desired amount of bone to be resected from the distal femoral condyle as indicated form the radiograph(s) in accordance with the method of the invention. One the assembled apparatus has been locked into position and/or pinned into place, cutting block 634 is coupled to component 630, and a cutting tool such as oscillating saw 720 is used to resect the distal femur (FIG. 7C), resulting in a balanced knee without the need for expensive computer navigation.

Note that the components may be provided in various sizes to suit different patient physiologies, and that block 604 along with plates 606, 608 may be removed from rods 614, 616 and flipped vertically to accommodate both the right and left knees.

Figure 8A:
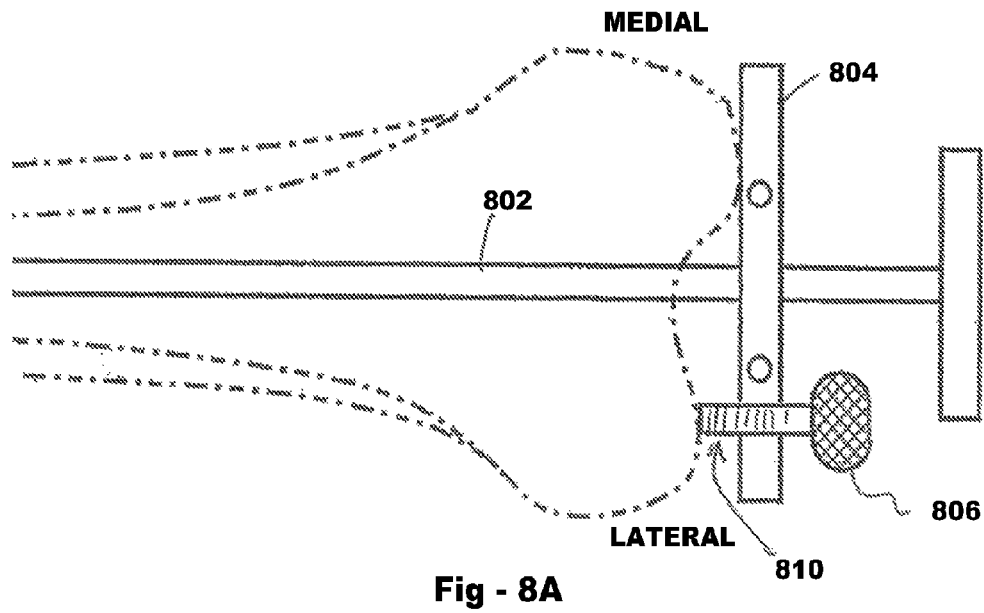
FIG. 8A is a top-down view of an embodiment of the invention which uses an an intramedullary rod.
Figure 8B:
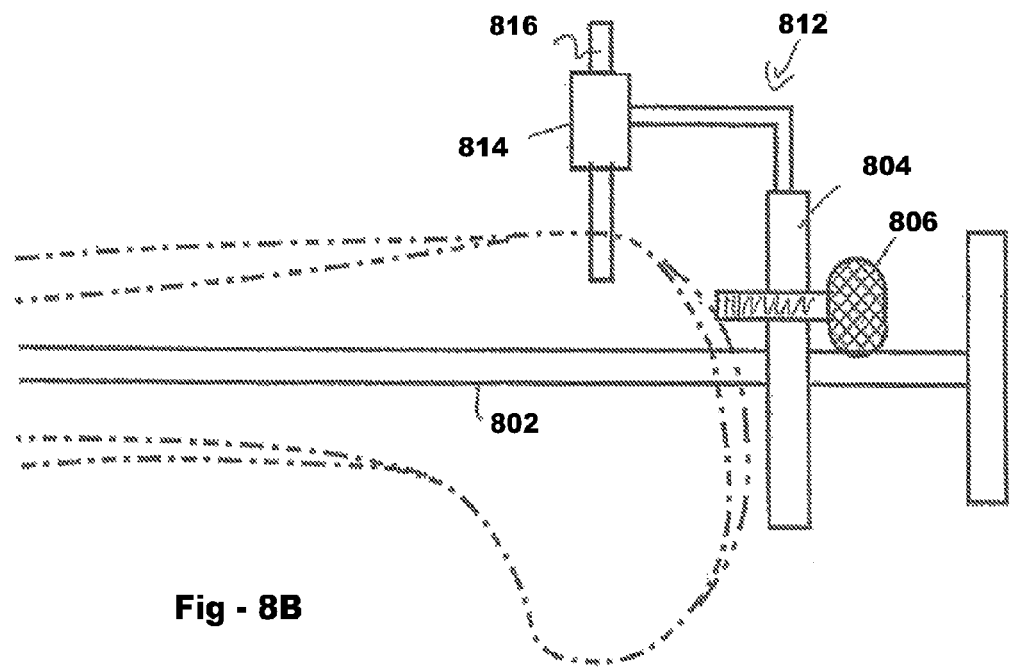
FIG. 8B is a side view of the embodiment shown in FIG. 8A.

While the embodiments thus far described do not require an intramedullary rod, FIGS. 8A and 8B depict an embodiment of the invention which uses an 1M rod 802. FIG. 8A is a top-down view, whereas FIG. 8B is a side view. An adjustable plate 804 slides along rod 802, the plate including an adjustment knob or device 806. The plate 804 makes direct contact with the distal femur on the medial side. By adjusting device 806 on the lateral side, the amount of bone resection may be varied. Manipulation of the device 806 results in a precise, controlled movement of the lateral side of the plate 804 toward/away from the apex of the condyle. For example, one turn of the device 806 may result in a millimeter of relative movement, with the measured amount being readable at 810. After the proper level has been determined, the cutting block is pinned to the distal femur and a cut is made. FIG. 8B shows a link 812 coupling the plate 804 to a body 814 and pin 816. The link may be removed after the block 804 is pinned in position.

I claim:

1. A cutting fixture for total knee replacement surgery, comprising:
    a contact plate having a surface adapted for placement against the apex of a distal femur having medial and lateral condyles;
    a body including an adjustment mechanism enabling the body to assume an angle relative to the contact plate;
    a cutting block coupled to the body to resect a predetermined thickness from the medial condyle and an amount from the lateral condyle determined through measurement of an x-ray or CT image of the femur;
    an anchoring device for holding the fixture in position to resect the medial and lateral condyles; and
    an indicator showing the angle between the contact plate and the body.

2. The cutting fixture of claim 1, wherein the body is also slideable relative to the contact plate.

3. The cutting fixture of claim 1, wherein the anchoring device is a foot adapted for placement against the cortex of a femur or an intramedullary rod.

4. The cutting fixture of claim 1, wherein the resections of the medial and lateral condyles are substantially perpendicular to the mechanical axis of the femur also determined from the x-ray or CT scan.

5. The cutting fixture of claim 1, wherein:
    the surface of the contact plate is adapted for placement against the apex of a medial condyle; and
    the resection of the lateral condyle is in the range of 3-4 mm less than the resection of the medial condyle.

6. The cutting fixture of claim 1, wherein at least portions of the fixture may be turned upside-down for use with right and left knee replacements.

* * * * *